United States Patent
Mason

(10) Patent No.: US 6,835,742 B2
(45) Date of Patent: Dec. 28, 2004

(54) SYNERGISTIC EFFECT OF AMLODIPINE AND ATORVASTATIN ON CHOLESTEROL CRYSTAL FORMATION INHIBITION AND AORTIC ENDOTHELIAL CELL NITRIC OXIDE RELEASE

(76) Inventor: R. Preston Mason, P.O. Box 418, Manchester, MA (US) 01944

( * ) Notice: Subject to any disclaimer, the term of this patent is extended or adjusted under 35 U.S.C. 154(b) by 147 days.

(21) Appl. No.: 09/921,479

(22) Filed: Aug. 3, 2001

(65) Prior Publication Data

US 2002/0052394 A1 May 2, 2002

Related U.S. Application Data

(60) Provisional application No. 60/223,214, filed on Aug. 4, 2000.

(51) Int. Cl.$^7$ ......................... A61K 31/44; A61K 31/40
(52) U.S. Cl. ..................... 514/356; 514/354; 514/408; 514/422; 514/423
(58) Field of Search ................. 514/354–356, 514/408, 422, 423, 330; 546/229; 548/530

(56) References Cited

U.S. PATENT DOCUMENTS

| | | |
|---|---|---|
| 4,879,303 A | 11/1989 | Davison et al. |
| 6,262,092 B1 * | 7/2001 | Chang et al. ............... 514/356 |
| 6,455,574 B1 * | 9/2002 | Buch .......................... 514/427 |
| 2002/0086889 A1 * | 7/2002 | Mason ....................... 514/355 |

FOREIGN PATENT DOCUMENTS

WO    WO 99/11259    3/1999

OTHER PUBLICATIONS

J. Wouter Jukema, et al.; "Evidence for a Synergistic Effect of Calcium Channel Blockers with Lipid–Lowering Therapy in Retarding Progression of Coronary Atherosclerosis in Symptomatic Patients with Normal to Moderately Raised Cholesterol Levels"; Arteriosclerosis, Thrombosis, and Vascular Biology. 1996; 16:425–430.

Bertram Pitt, et al.; "Effect of Amlodipine on the Progression of Atherosclerosis and the Occurrence of Clinical Events"; Circulation, 2000; 102.1503–1510.

* cited by examiner

Primary Examiner—Dwayne Jones
(74) Attorney, Agent, or Firm—Perkins Smith & Cohen, LLP; Stephen J. Gaudet

(57) ABSTRACT

The combination of the antihypertensive calcium channel blocker amlodipine and lipid-lowering agent atorvastatin inhibits free cholesterol crystallization in atherosclerotic-like membranes. In addition, treatment with a combination of amlodipine and atorvastatin results in a synergistic effect on the release of NO from rabbit aorta endothelial cells.

24 Claims, 7 Drawing Sheets

SYNERGISTIC EFFECT OF AMLODIPINE AND "COMPOUND T" ON NITRIC OXIDE STIMULATION IN RABBIT AORTA

"Compound T" = Atorvastatin calcium

"Compound T" = Atorvastatin calcium

SYNERGISTIC EFFECT OF AMLODIPINE AND ATORVASTATIN ON CHOLESTEROL CRYSTAL FORMATION INHIBITION AND AORTIC ENDOTHELIAL CELL NITRIC OXIDE RELEASE

CROSS-REFERENCE TO RELATED APPLICATIONS

This application claims priority from U.S. Provisional Patent Application No. 60/223,214 entitled "Synergistic Effect of Amlodipine and Atorvastatin on the Stimulation of Nitric Oxide Release from Rabbit Aorta Endothelial Cells" that was filed on Aug. 4, 2000.

FIELD OF THE INVENTION

This invention relates to the effect of amlodipine and atorvastatin, alone and in combination, on cholesterol crystal formation and the release of nitric oxide (NO) from endothelial cells.

BACKGROUND OF THE INVENTION

Coronary artery disease (CAD) is the leading cause of mortality in the developed world, and is associated with substantial morbidity as well. Typically, the patient with CAD has several concomitant conditions, including hypertension, diabetes, and dyslipidemia, increasing overall risk for poor outcomes and complicating treatment. A therapeutic goal for the treatment of CAD is the development of drugs that can simultaneously target multiple underlying disease processes that contribute to atherosclerosis, thereby altering the course of the disease. Therefore, CAD therapy may have increased positive outcomes if the use of an antihypertensive agent and HMG-CoA reductase inhibitor was combined in a single delivery system.

Free cholesterol is an important structural component of the cell plasma membrane that modulates packing of phospholipid molecules, thus regulating lipid bilayer dynamics and structure. The cholesterol molecule is oriented in the membrane such that the long-axis lies parallel to the phospholipid acyl chains, increasing order in the upper acyl chain region of the membrane while decreasing packing constraints at the terminal methyl groups. During atherogenesis, however, increasing levels of cellular cholesterol lead to its abnormal deposition in the vessel wall and the formation of cholesterol crystals.

In animal models of atherosclerosis, it has been demonstrated that the cholesterol content of membranes associated with vascular smooth muscle and macrophage foam cells becomes elevated, resulting in the formation of discrete domains. These highly organized cholesterol structures, characterized by a unit cell periodicity of 34.0 Å, appear to serve as nucleating sites for the formation of extracellular crystals. These domains have been previously described in model membrane systems. A recent study from our laboratory showed that cultured mouse peritoneal macrophage foam cells produced free cholesterol crystals that extend from intracellular membrane sites with various morphologies that include plates, needles and helices. With the use of x-ray diffraction approaches, the early stages of crystal formation could be identified in isolated membranes from these cells. Preventing crystal formation is an important goal as cholesterol in this state is practically inert and does not respond well to pharmacologic interventions that promote lesion regression.

In addition, the normal production of NO by the endothelium is critical for maintaining vascular function. During atherosclerosis, however, endothelial dysfunction effects a significant reduction in NO production, resulting in: 1) increased monocyte and LDL infiltration, 2) loss of smooth muscle cell function and abnormal proliferation, 3) increased oxidative stress, and 4) increased platelet aggregation. Pharmacologic interventions that restore endothelial function and NO metabolism have demonstrated benefit in the treatment of various cardiovascular disorders, including coronary artery disease.

However, no pharmaceutical composition currently exists that treats both hypertension and hyperlipidemia. Such a pharmaceutical composition would have several benefits. For example, the multiple risk factors for arterial and related heart disease that are often present in an individual patient could be targeted simultaneously. Additionally, the ease of taking one combined dosage could significantly enhance patient compliance with therapeutic regimens.

Therefore, it is an object of this invention to provide a combination therapy that will treat the multiple pathological processes involved in arterial and related heart disease. These include, but are not limited to, hypertension and hyperlipidemia. It is also an object of this invention to develop useful and convenient dosage levels and forms of such a combination therapeutic. Preferably, this pharmaceutical composition would have synergistic effects on these hallmarks of arterial and related heart disease, such that the individual effects of the components of this composition would be enhanced by their combination.

Thus, this invention encompasses a therapeutic goal for the treatment of CAD that entails the development of drugs that can simultaneously target multiple underlying disease processes that contribute to atherosclerosis, thereby altering the course of the disease. Therefore, using this invention, CAD therapy may have increased positive outcomes if the use of an antihypertensive agent and HMG-CoA reductase inhibitor was combined in a single delivery system.

SUMMARY OF THE INVENTION

Lipophilic agents that influence the organization of lipids may interfere with the early formation of cholesterol domains within the membrane, thereby disrupting crystal formation. The charged dihydropyridine amlodipine (AML) was used for this study as it has strong affinity for phospholipid constituents of atherosclerotic-like membranes, as compared to other calcium channel blockers (CCBs). This property of the drug is attributed to a distinct membrane location that facilitates strong electrostatic binding to the phospholipid phosphate groups, as indicated by x-ray diffraction, differential scanning calorimetry and nuclear magnetic resonance analyses. These distinct membrane interactions may underlie the ability of AML to reverse cholesterol-induced increases in the width of atherosclerotic membranes obtained from vascular smooth muscle cells and to interfere with oxidative modification of lipid constituents.

The various membrane biophysical effects of AML may contribute to its observed benefit in coronary artery disease, as demonstrated in the Prospective Randomized Evaluation of the Vascular Effects of Norvasc Trial (PREVENT). The results of PREVENT showed a reduction in cardiovascular morbidity associated with AML therapy, including a 42% reduction in the need for revascularization and 33% reduction in documented angina, as compared to placebo. AML therapy was also associated with significant slowing in the progression of carotid atherosclerosis, as measured with B-mode ultrasonographic assessments. As such clinical benefit has not been observed with other CCB analogs in similarly designed trials, it has been proposed that AML may have distinct antiatherosclerotic activity.

Hypolipidemic therapy has also been demonstrated to be very useful in reducing morbidity and mortality associated with CAD. Among HMG-CoA reductase inhibitors, atorvastatin calcium (AT) has been shown to be very effective as hypolipdemic therapy. In a recent clinical study involving patients with stable and advanced CAD, aggressive lipid-lowering therapy with AT significantly delayed the time to a first ischemic event and reduced, by 36%, the overall incidence of cardiovascular events, as compared to angioplasty with usual medical care.

Small angle x-ray diffraction approaches were utilized to examine the separate and combined effects of AML and AT on the formation of cholesterol monohydrate structures (d-space of 34.0 Å) within the membrane bilayer. This question was investigated in membranes containing cholesterol at levels that reproduce atherosclerotic-like conditions. The results of this study demonstrated that these compounds interfered with the aggregation of cholesterol into separate intrabilayer domains in an unexpected and highly synergistic fashion. This observed effect could not be reproduced by the combination of these compounds with other related drugs. By disrupting the development of cholesterol crystals, this drug combination may facilitate the removal of excess sterol from the vessel wall by plasma high-density lipoproteins (HDL).

In addition, NO production from endothelial cells in rabbit aorta was systematically measured in the absence and presence of amlodipine, atorvastatin, and the combination of the two compounds. The results of these experiments demonstrated a dramatic synergistic effect of these compounds on NO stimulation. These findings indicate that these agents may effectively stabilize, in a synergistic fashion, NO in the cell by interfering with oxidative destruction.

Other objects, features, and advantages of the present invention will be apparent from the following Detailed Description of the Preferred Embodiments taken in conjunction with the accompanying drawings in which:

BRIEF DESCRIPTION OF THE DRAWINGS

In FIG. 2A, the effect of temperature on membrane width was evaluated at a constant 93% relative humidity while in FIG. 2B the effect of relative humidity was measured at a constant temperature of 20° C. These data demonstrate that the structure of the cholesterol monohydrate crystalline domains (34.0 Å) are unaffected by changes in temperature or humidity, as compared to the surrounding sterol-poor region of the membrane.

DETAILED DESCRIPTION OF THE PREFERRED EMBODIMENTS

Experimental Methods

Figure 1:
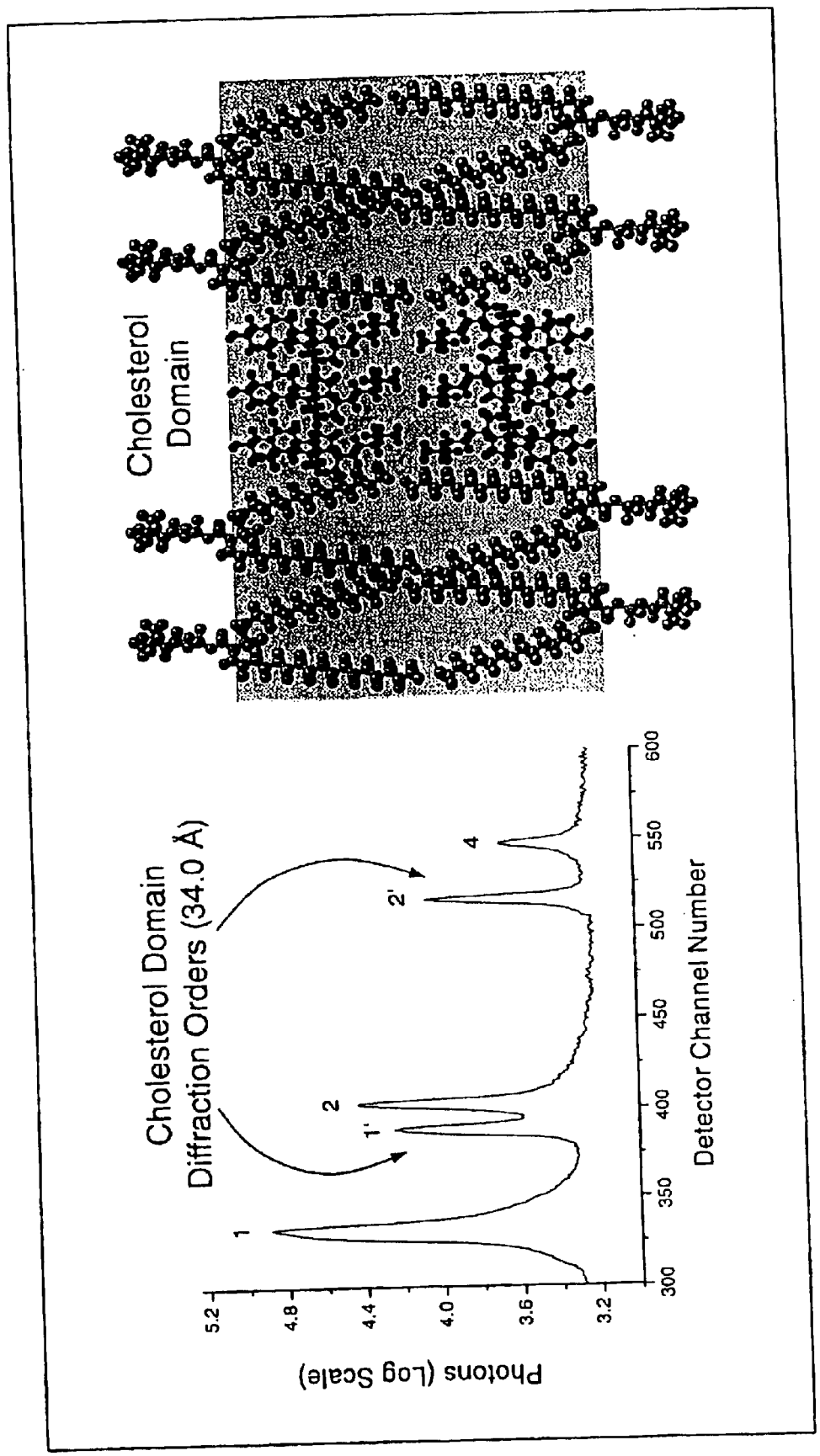
FIG. 1 shows the X-ray diffraction pattern and corresponding molecular model for cholesterol-enriched membrane bilayer. Diffraction peaks corresponding to sterol-rich and -poor domains can be clearly distinguished at 87% relative humidity at 20° C. The peaks labeled 1' and 2' correspond to the sterol-rich domain (d=34.0 Å) while the surrounding sterol-poor area of the membrane had a d-space value of 60.7 Å, corresponding to peaks labeled 1, 2 and 4. The corresponding molecular model demonstrates cholesterol bilayer domain with a dimension of 34.0 Å (each individual cholesterol monohydrate molecule is 17.0 Å) that is highlighted by the shaded region of the figure.

Preparation of reconstituted membrane samples. Porcine cardiac phospholipid dissolved in HPLC-grade chloroform (10.0 mg/ml) was obtained from Avanti Polar Lipids Inc. (Alabaster, Ala.) and stored at −80° C. The fatty acid composition of the phosphatidylcholine lipids was determined by gas-liquid chromatographic analysis. The overall ratio of saturated to unsaturated fatty acids was 0.8:1, with the primary constituents being 18:2 linoleic acid (30%), 16:0 palmitic acid (22%), 18:1 oleic acid (13%), and 20:4 arachidonic acid (11%). Cholesterol powder was also purchased from Avanti Polar Lipids Inc. Amlodipine besylate (AML) was obtained from Pfizer Central Research (Groton, Conn.) while atorvastatin calcium (AT) was provided by Parke Davis (Ann Arbor, Mich.).

The effects of the drugs on membrane cholesterol organization and structure were assessed in well-defined lipid vesicles containing equimolar levels of cholesterol and phospholipid. This reconstituted membrane system was used for the following reasons: 1) this system reproduces changes in membrane structure observed in cholesterol-enriched, atherosclerotic macrophage and smooth muscle cell membranes, 2) the membrane preparation does not contain calcium channels, and 3) these samples can be prepared in a highly reproducible fashion. Lipid vesicles were formed from phospholipid and cholesterol dissolved in chloroform at a fixed molar ratio and added to individual glass 13×100-mm test tubes. The chloroform solvent was removed by shell-drying under a steady stream of $N_2$ gas. Residual solvent was removed under vacuum while the samples were shielded from light. Membrane vesicles were produced for diffraction analysis by rapidly mixing the dried lipids at room temperature following addition of buffered saline (0.5 mmol/L HEPES and 154.0 mmol/L NaCl, pH, 7.2). The final phospholipid concentration was 5.0 mg/ml. Membrane samples were oriented for diffraction analysis by centrifugation and then placed in hermetically sealed canisters that controlled temperature and relative humidity, as previously described.

Small angle x-ray diffraction analysis. Small-angle x-ray diffraction approaches were used to directly examine the effects of the various drugs on the organization of cholesterol in the membrane. X-ray diffraction experiments were conducted by aligning the samples at grazing incidence with respect to a collimated, nickel-filtered monochromatic x-ray source ($CuK_\alpha$=1.54 Å) produced by a high-brilliance rotating anode microfocus generator (Rigaku Rotaflex RU-200, Danvers, Mass.). The diffraction data were collected on a one-dimensional, position-sensitive electronic detector (Innovative Technologies, Newburyport, Mass.) placed at a distance of 150 mm from the sample. In addition to direct calibration of the detector system, cholesterol monohydrate crystals were used to verify the calibration, as previously described. The unit cell periodicity, or d-space, of the membrane lipid bilayer is the measured distance from the center between one bilayer to the next, including surface hydration, and calculated from Bragg's Law.

NO release measurements. All measurements presented were recorded in vitro. NO release was measured directly from a single endothelial cell in the rabbit aorta. Measurements were done in Hank's balance solution at 37° C. A porphyrinic sensor (diameter 0.2±0.1 $\mu$m) was placed near the surface (10±5 $\mu$m) of the endothelial cells using a computer controlled micromanipulator. The sensor operated with a three-electrode system [sensor working electrode, platinum wire (0.1 mm) counter electrode, and saturated calomel electrode (SCE—reference electrode)]. The three electrodes were connected to a potentiostat/galvanostat PAR273. Data were acquired with the use of an IBM computer with custom software. The current proportional to NO concentration was measured by porphyrinic sensor, which operated in amperometric mode at constant potential of 0.63 V vs. SCE.

The release of NO was initiated by the injection of potential agonists of endothelial NO synthase (eNOS) using a temtoinjector placed in the controlled distance from the endothelial cell. Two different agonists were tested: amlodipine and atorvastatin. The different concentrations of these two compounds applied simultaneously were also tested.

Atherosclerotic-like membranes have distinct crystalline-like sterol domains: Membrane sterol-rich domains may represent an important nucleating site for free cholesterol crystal formation, an important feature of the unstable plaque. The separate and combined effects of AML and AT on cholesterol monohydrate formation in membranes reconstituted from native phospholipids isolated from cardiac tissue was evaluated. Phospholipid composed of heterogeneous acyl chains was used for these analyses. This membrane system reproducibly formed discrete sterol-rich domains at levels previously observed in atherosclerosis studies under similar experimental conditions.

X-ray diffraction analysis of oriented, cholesterol-enriched membranes produced strong, reproducible diffraction orders that correspond to structurally distinct sterol-rich and -poor membrane regions. The d-space measurement refers to the average distance from the center of one membrane bilayer to the next, including surface hydration. The d-space of the sterol-rich region was 34.0 Å, indicative of a cholesterol bilayer structure as a single cholesterol monohydrate molecule has a long axis of 17 Å (FIG. 1). The surrounding sterol-poor regions, meanwhile, had an average width of 65.9 Å at 20° C. and 93% relative humidity. The much larger width (>90%) of the sterol-poor domains is attributed to the abundance of phospholipid in the surrounding membrane region. The cholesterol domains were invariably present over a wide range of temperatures (5–37° C.) and relative humidity levels (74–93%), consistent with previous x-ray diffraction analyses on atherosclerotic-like membrane samples.

Figure 2:
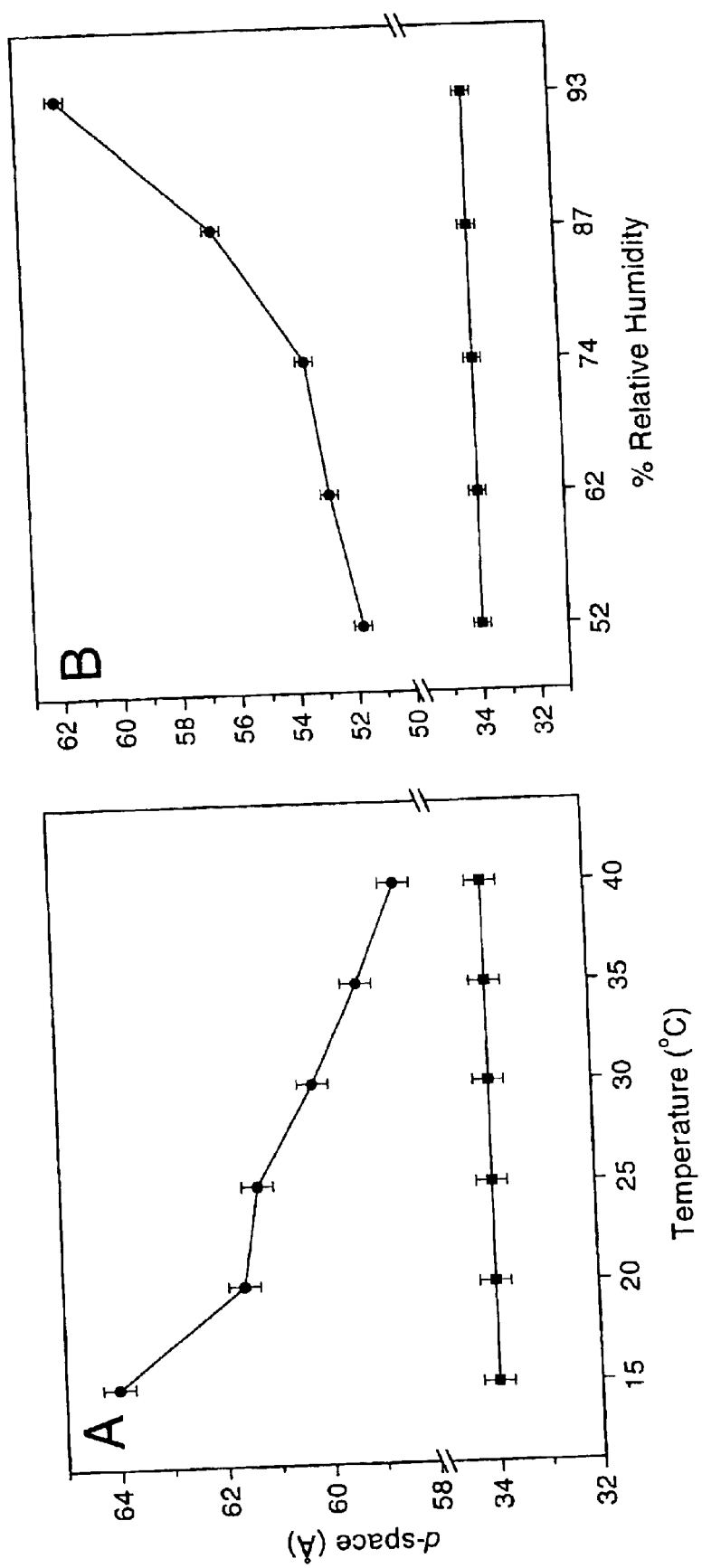
FIG. 2 shows the differential effects of temperature (FIG. 2A) and relative humidity (FIG. 2B) on the molecular dimensions of cholesterol monohydrate domains versus surrounding sterol-poor membrane regions for samples containing verapamil. The membrane width, as measured in Å units by x-ray diffraction analysis, represents the distance from the center of one membrane to the next, including surface hydration.

In FIG. 1, diffraction peaks corresponding to the sterol-rich and -poor domains can be clearly distinguished at 20° C. The peaks labeled 1' and 2' correspond to the sterol-rich domain (d=34.0 Å) while the surrounding sterol-poor area of the membrane had a d-space value of 60.7 Å, corresponding to peaks labeled 1, 2 and 4. The peaks that describe the cholesterol monohydrate phase are very sharp, as expected for a crystalline-like structure. In every sample that was evaluated, it was observed that the dimensions of the sterol-poor region of the membrane was modulated by temperature and relative humidity due to its heterogeneous chemical composition and the dynamic mobility of the phospholipid-cholesterol binary mixture. At 93% relative humidity, for example, the d-space of the sterol-poor region decreased by 5.5 Å (9%) as sample temperature was increased from 15° C. (64 Å) to 40° C. (58.5 Å), consistent with increased trans-gauche isomerizations (FIG. 2). Over this same temperature range, however, the cholesterol monohydrate phase remained unchanged at 34.0 Å, as expected for a crystalline-like structure. In addition, the highly reproducible 34.0 Å structure was unaffected by large changes in relative humidity (52 to 93%) at 20° C. while the sterol-poor region changed by 19% or 10 Å (52 to 62 Å) over this same range.

Figure 3:
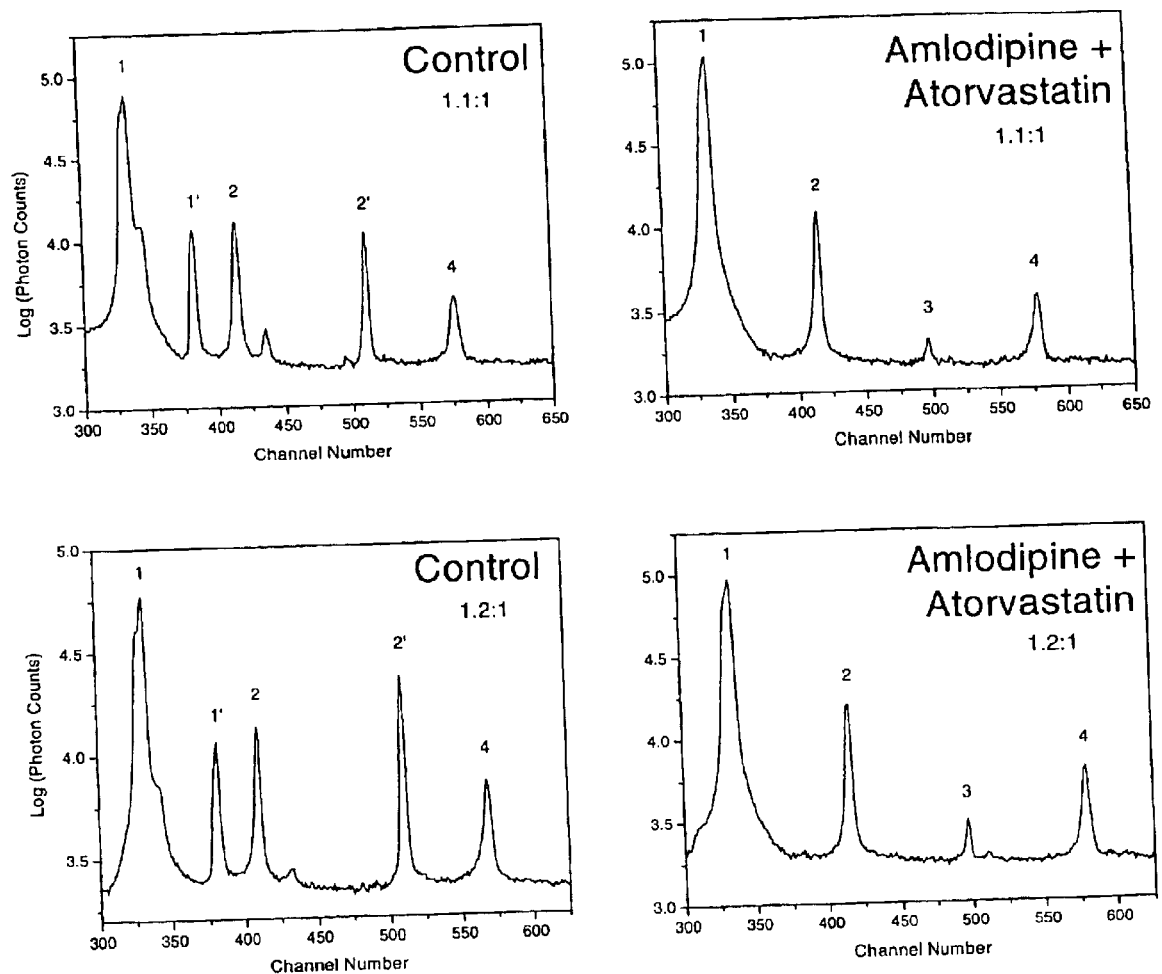
FIG. 3 shows the X-ray diffraction pattern from oriented membrane lipid bilayers containing elevated levels of cholesterol (1.1:1 and 1.2:1 cholesterol to phospholipid mole ratios) prepared in the absence or presence of the AML/AT combination at 5° C. At a 1.1:1 cholesterol to phospholipid mole ratio, peaks labeled 1, 2 and 4 correspond to d-space values of 54.2 Å and 53.0 Å, respectively, for the control and drug-containing samples. At a 1.2:1 cholesterol to phospholipid mole ratio, peaks labeled 1 and 2 corresponded to d-space values of 55.5 Å and 53.5 Å, respectively, for the control and drug-containing samples. This figure demonstrates that at a low concentration (30 nM), the combination of AML and AT completely blocked the aggregation of cholesterol into discrete cholesterol domains.

Synergistic inhibition of sterol domain formation with amlodipine and atorvastatin: The addition of both AML and AT to cholesterol-enriched membrane samples prevented sterol domain formation in a synergistic fashion. At an aqueous buffer concentration of 30 nM, the combination of AML and AT completely blocked the formation of cholesterol domains in membrane samples containing cholesterol and phospholipid at 1.1:1 and 1.2:1 cholesterol:phospholipid mole ratios. In the presence of the two drugs, only peaks corresponding to the phospholipid bilayer could be observed under a variety of experimental conditions, as compared to control (FIG. 3). At a 1.1:1 mole ratio, the d-space values for the control and drug combination-containing samples were 54.2 and 53.9 Å, respectively, at 74% relative humidity and 5° C. At a 1.2:1 mole ratio, the d-space values for the control and drug combination-containing samples were 55.5 and 53.5 Å, respectively, at 74% relative humidity and 5° C.

Figure 4:
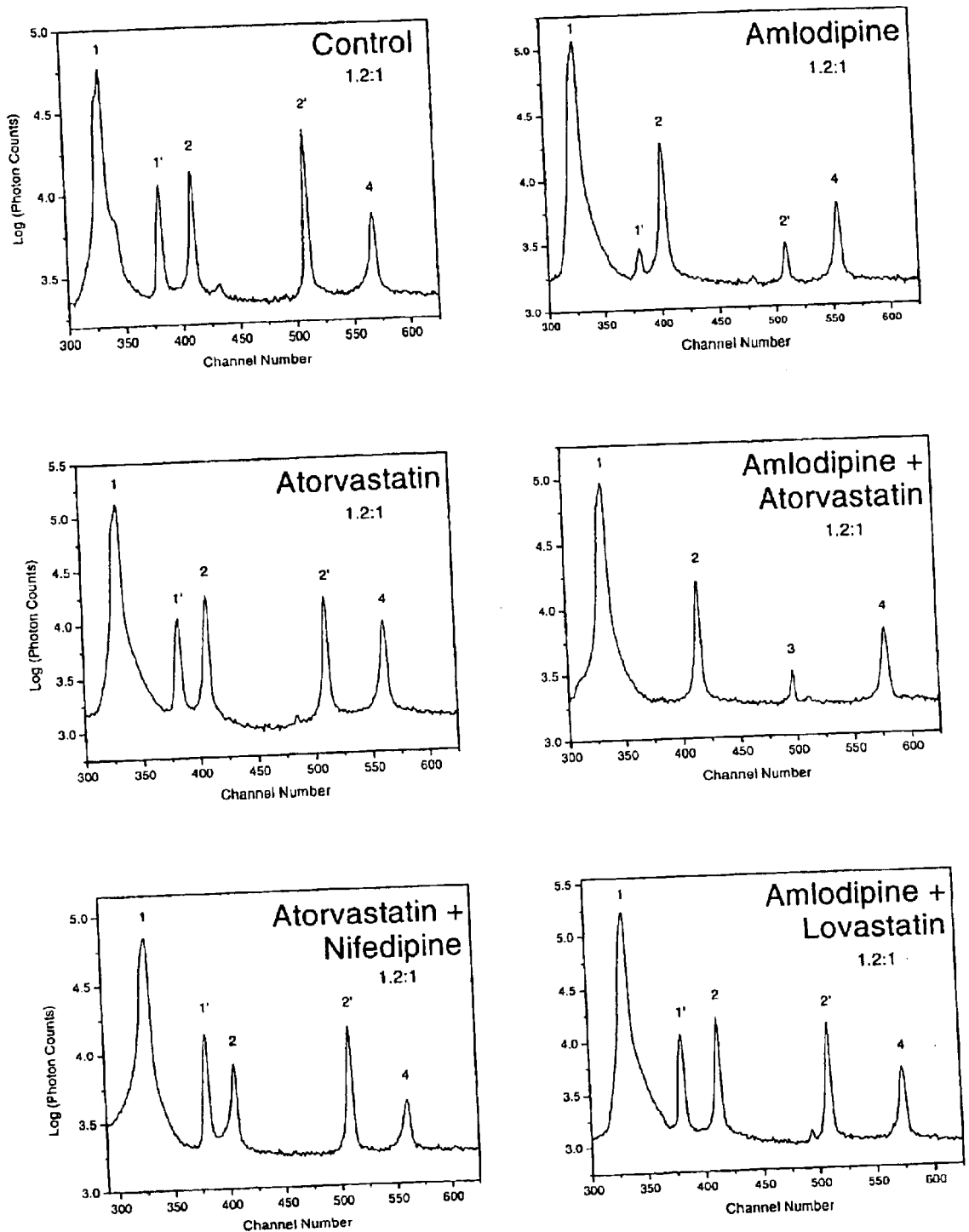
FIG. 4 shows the X-ray diffraction patterns from oriented membrane lipid bilayers containing elevated levels of cholesterol (1.2:1 cholesterol to phospholipid mole ratio) prepared in the absence or presence of AML alone, AT alone, AML/AT combination, AT/nifedipine combination, and AML/lovastatin combination at 5° C. The peaks labeled 1, 2 and 4 correspond to the sterol-poor region of the membrane while peaks labeled 1' and 2' correspond to the structure of cholesterol monohydrate domains within the membrane (34.0 Å). The dimensions of the surrounding sterol-poor regions were as follows: control (55.5 Å), AML alone (57.8 Å), AT alone (56.8 Å), AML/AT (53.5 Å), AT/nifedipine (56.5 Å) and AML/lovastatin (54.4 Å). These experiments demonstrated that the ability of the AML/AT combination to interfere with membrane cholesterol domain formation could not be reproduced by the drugs separately or other CCB/statin combinations.

When AML or AT were added separately to the membrane samples, cholesterol domains could be clearly detected under identical conditions with small angle x-ray diffraction approaches. Moreover, the combination of AML and AT with other drugs had no inhibitory effect on cholesterol crystal formation. Both the combination of AML with the HMG-CoA reductase inhibitor lovastatin and the combination of AT with the CCB nifedipine failed to interfere with cholesterol domain formation, as compared to control samples (FIG. 4). Cholesterol domains were very prominent in these samples with a unit cell periodicity of 34.0 Å. These discrete structures coexist with the surrounding sterol-poor region of the membrane. At 5° C. and 74% relative humidity, the surrounding sterol-poor region of the membrane samples had the following d-space values: control (55.5 Å), AML/lovastatin (54.4 Å), and AT/nifedipine (56.5 Å). Finally, when AML and AT were added separately to the cholesterol-enriched membrane samples, they did not interfere with domain formation.

Figure 5:
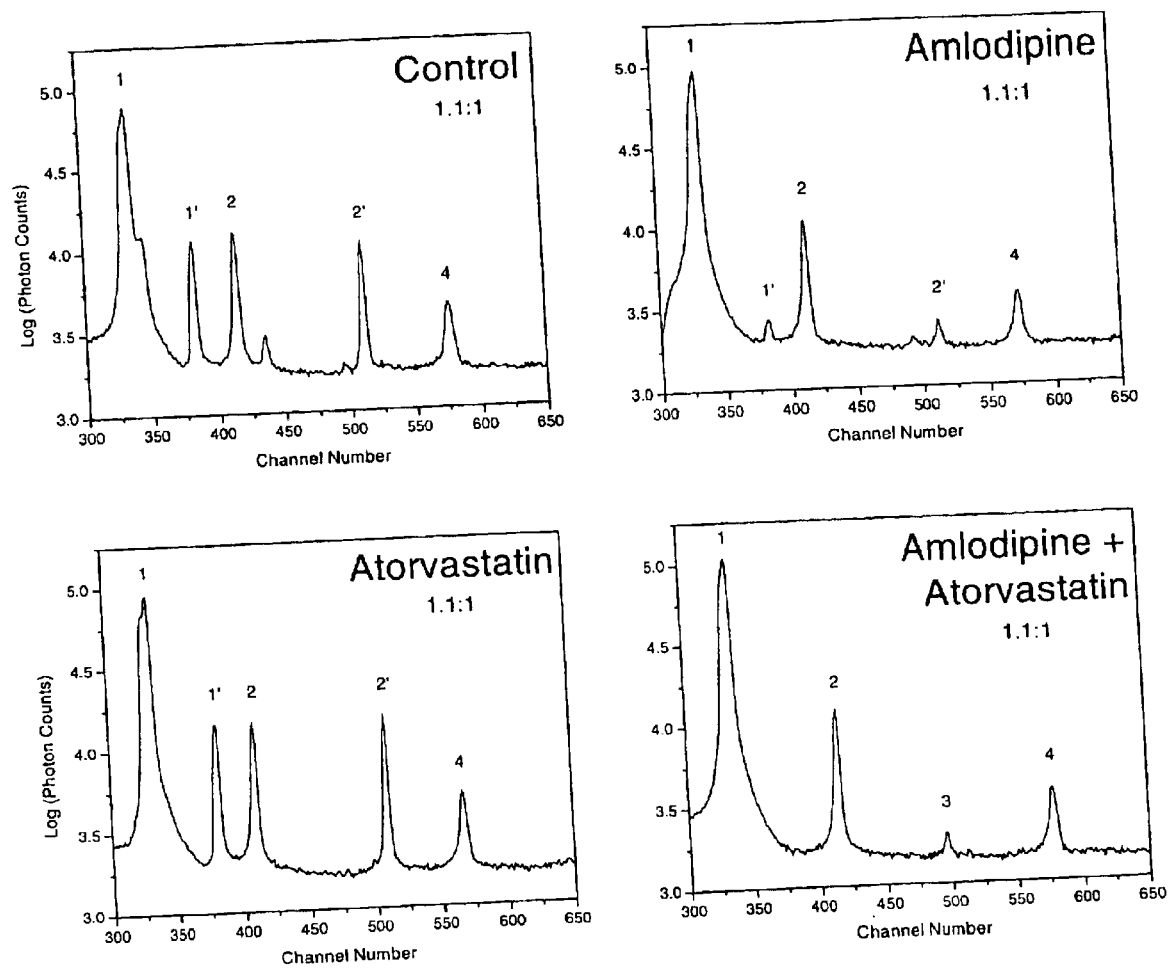
FIG. 5 shows the X-ray diffraction patterns from oriented membrane lipid bilayers containing elevated levels of cholesterol (1.1:1 cholesterol to phospholipid mole ratio) prepared in the absence or presence of AML alone, AT alone, and AML/AT combination at 5° C. The peaks labeled 1, 2 and 4 correspond to the sterol-poor region of the membrane while peaks labeled 1' and 2' correspond to the structure of cholesterol monohydrate domains within the membrane (34.0 Å). The dimensions of the surrounding sterol-poor regions were as follows: control (52.4 Å), AML alone (54.4 Å), AT alone (55.8 Å), and AML/AT (53.9 Å). These experiments demonstrated that the AML/AT combination was able to interfere with membrane cholesterol domain formation in a manner that could not be reproduced by the drugs separately.

The synergistic effect of AML and AT on cholesterol domain formation was also observed at a lower concentration of cholesterol. At a cholesterol to phospholipid mole ratio of 1.1:1, the drug combination effectively interfered with cholesterol crystallization within the membrane samples (FIG. 5). By contrast, when used separately, the drugs had no effect on domain formation, even at this lower level of membrane cholesterol. At 5° C. and 74% relative humidity, the surrounding sterol-poor region of the membrane samples had the following d-space values: control (55.5 Å), AML alone (54.4 Å), AT alone (55.8 Å), and AML/AT (53.9 Å).

An explanation for the synergistic effect of AML and AT on the organization of cholesterol may be their chemical properties. AML has very high lipophilicity as compared to other CCBs and a formal positive charge at physiologic pH. An electrostatic interaction between AML and AT as well as the phospholipid headgroup region of the membrane contributes to the high affinity of this agent for the lipid bilayer. Moreover, the charged amino-ethoxy function of AML directs the drug to a region of the membrane that overlaps the steroid nucleus of cholesterol molecules, an effect that may directly lead to a disruption in the self-association of cholesterol molecules in the membrane. Likewise, it has been observed that AT partitions to a similar location in the membrane as AML.

The key finding was the observation that the combination of AML and AT inhibited the formation of separate cholesterol domains in atherosclerotic-like membranes in a synergistic fashion. This biophysical effect of the drug combination was directly characterized with small angle x-ray diffraction approaches using lipid membranes enriched with cholesterol. As cholesterol aggregates within the membrane may serve as nucleating sites for extracellular free cholesterol crystal formation in the vessel wall, the ability of the AML/AT combination to block such sterol domain formation indicates a novel antiatherosclerotic mechanism of action. This observed effect appears to be distinct for these drugs as other combinations failed to reproduce this change in the aggregation properties of free cholesterol.

In atherosclerosis, the incidence of lesion rupture and thrombosis is affected by the lipid composition of the atherosclerotic plaque. The lipid component of atherosclerotic lesions consists primarily of cholesterol and phospholipid, with lesser amounts of fatty acid and triacylglycerol. Over time, cholesterol forms crystalline structures in the human atheroma, an event that contributes to overall lesion mass and plaque instability. Once crystallized, cholesterol within the lesion is essentially inert and cannot be effectively removed by lipoprotein acceptors in the plasma. By contrast, non-crystallized cholesterol associated with foam cell membranes or intracellular stores can be depleted by plasma HDL and pharmacological interventions, leading to lesion regression.

Recent reports indicate that the cellular membrane is a cellular site for free cholesterol accumulation, leading to discrete sterol-rich domains and eventually crystal. In macrophage foam cells, for example, a critical mass of cholesterol is achieved following lipoprotein (native or oxidized) uptake and/or phagocytosis of lipid released from neighboring necrotic foam cells. Ultimately, a nucleating event will occur at a critical concentration of cholesterol enrichment, leading to cholesterol domain development within the membrane. By interfering with the formation of highly organized cholesterol aggregates within the membrane, the combination of AML and AT may significantly slow or even prevent subsequent crystal development in the vessel wall, and thereby block the progression of an otherwise irreversible step in atherosclerosis. Moreover, these agents may work synergistically with HDL and lipid-lowering therapy in reducing the accumulation of cholesterol crystals in the wall of the diseased artery by maintaining cholesterol in a non-crystalline or dynamic state in cellular membranes.

The mechanism by which AML and AT interfere with the aggregation of cholesterol into discrete domains may be related to its their molecular membrane interactions. At physiologic pH, more than 90% of the amino ethoxy function associated with the #2 position of the dihydropyridine ring of AML is in the charged state. This positive charge contributes to specific electrostatic interactions of AML with phosphate groups associated with the phospholipid bilayer surface. The results of previous small-angle x-ray diffraction, differential scanning calorimetry and nuclear magnetic resonance analyses support a molecular model that places the charged amino function of AML near oppositely charged groups in the phospholipid headgroup region. Simultaneously, the hydrophobic portion of the dihydropyridine molecule is buried within the membrane hydrocarbon core, adjacent to the headgroup region. These biophysical measurements indicate that the time-averaged location of the ring structure for AML overlaps the sterol nucleus of cholesterol in the membrane, where it can then modulate certain biophysical effects of the molecule, and interfere with its self-association. Likewise, small-angle x-ray diffraction approaches demonstrated that AT partitioned to a discrete location in the membrane bilayer.

Thus, this unexpected, synergistic effect can be attributed to the molecular interactions of these compounds with membrane lipid constituents. This finding has important relevance for the treatment of coronary artery disease (CAD) as this disorder is characterized by the abnormal accumulation of free cholesterol into separate, membrane domains (d-space of 34.0 Å). These domains disrupt cellular function and lead to extracellular crystal formation, an important feature of the unstable atherosclerotic plaque. Small angle x-ray diffraction analyses demonstrated, for the first time, that the combination of AML and AT blocked the aggregation of free cholesterol into crystalline-like domains at low, nanomolar concentrations. By contrast, the combination of these agents with other related drugs showed no inhibitory effect on cholesterol crystal formation. These findings indicate that the combination of AML and AT produces a novel antiatherosclerotic effect by disrupting cholesterol crystal formation in atherosclerotic-like membranes. By disrupting the formation of cholesterol crystals in the vessel wall, the AML/AT combination would reduce plaque instability while facilitating cholesterol efflux to sterol acceptor particles, such as HDL. This new antiatherosclerotic mechanism of action for the AML/AT combination would complement the separate activities of these agents in the effective treatment of cardiovascular disease.

Figure 6:
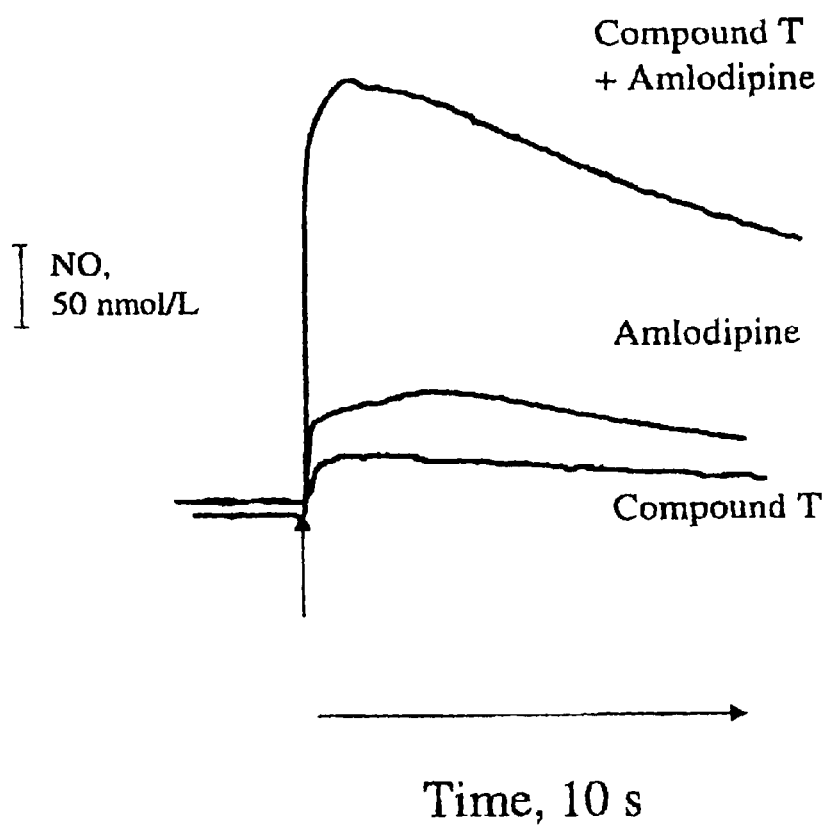
FIG. 6 shows the effect of amlodipine, atorvastatin (Compound T), and a mixture of the two compounds on NO release from a single rabbit aorta endothelial cell.

NO Release from Aortic Endothelial Cells: An amperogram (concentration of NO recorded versus time) obtained during amlodipine (5 $\mu$mol/L)-stimulated NO release from the single rabbit aorta endothelial cell is shown in FIG. 6. NO was released in the form of sinusoidal pulse with maximum concentration of 120±15 mmol/L. After the injection of atorvastatin, a small increase of NO concentration was also observed with maximum of 20±5 nmol/L. This concentration is very low and may be due to the process of scavenging of superoxide by atorvastatin (i.e., an increase of net basal NO production). The injection of 5 $\mu$mol/L of atorvastatin followed by the injection of 5 $\mu$mol/L of amlodipine caused a massive release of NO reaching a maximum of 300±10 mmol/L. The concentration of NO produced in association with the drug combination is twice what is expected based on the additive effects of the compounds, as recorded with separately with amlodipine or atorvastatin.

Figure 7:
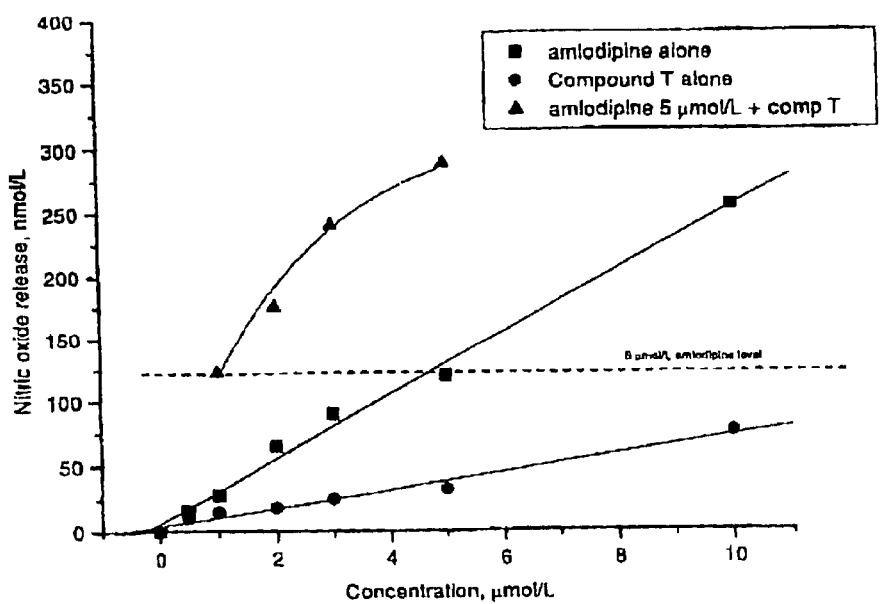
FIG. 7 shows the dose response curves for NO release stimulated by amlodipine, atorvastatin (Compound T), and a mixture of amlodipine with varying concentrations of atorvastatin (Compound T).

FIG. 7 shows dose response curves for NO release stimulated by amlodipine, atorvastatin, and the mixture of 5 $\mu$mol/L of amlodipine and variable concentrations (from 1–5 $\mu$mol/L) of atorvastatin. Based on the data from this Figure, there is a significant synergistic effect observed after stimulation of NO release from endothelial cells by the combination of amlodipine and atorvastatin over a range of doses.

Therefore, the results of these analyses demonstrated a powerful synergistic effect for the combination of amlodipine and atorvastatin on the inhibition of cholesterol crystal formation and nitric oxide release from rabbit aortic endothelial cells. The results of this study provide compelling scientific support for the combined use of AML and AT in the treatment of cardiovascular disorders. These novel antiatherosclerotic effects of the AML/AT combination complement the separate activities of these agents in the treatment of cardiovascular disease, including CAD.

It will now be apparent to those skilled in the art that other embodiments, improvements, details, and uses can be made that are consistent with the letter and spirit of the foregoing disclosure and within the scope of this patent and the appended claims.

What is claimed is:

1. A method of synergistically increasing nitric oxide production by endothelial cells comprising administering a therapeutically effective amount of a combination of amlodipine and an atorvastatin compound selected from the group consisting of atorvastatin and hydroxylated atorvastatin metabolite.

2. The method of claim 1 wherein amlodipine comprises a therapeutically effective derivative of amlodipine.

3. The method of claim 1 wherein the therapeutically effective derivative of amlodipine comprises amlodipine besylate.

4. The method of claim 1 wherein the atorvastatin compound comprises a therapeutically effective derivative of the atorvastatin compound.

5. The method of claim 4 wherein the therapeutically effective derivative of the atorvastatin compound is a hemicalcium salt.

6. The method of claim 1 wherein amlodipine and the atorvastatin compound are administered in the same therapeutic.

7. The method of claim 1 wherein amlodipine and the atorvastatin are administered as separate therapeutics.

8. The method of claim 1 wherein amlodipine and the atorvastatin compound are administered at the same time.

9. The method of claim 1 wherein amlodipine and the atorvastin compound are administered at different times.

10. The method of claim 1 wherein said pharmaceutical composition synergistically increases nitric oxide production by endothelial cells to an extent consistent with a reduced risk of arterial and related heart disease.

11. The method of claim 10 wherein said arterial and related heart disease is selected from the group consisting of hypertension, hyperlipdemia, atherosclerosis, arteriosclerosis, coronary artery disease, myocardial infarction, congestive heart failure, stroke, and angina pectoris.

12. The method of claim 1, wherein said atorvastatin compound is atorvastatin.

13. The method of claim 1, wherein said atorvastatin compound is hydroxylated atorvastatin metabolite.

14. A method of synergistically increasing nitric oxide production by endothelial cells comprising the administration of an effective amount of a combination of amlodipine and atorvastatin.

15. The method of claim 14, wherein said atorvastatin is a hydroxylated atorvastatin metabolite.

16. The method of claim 14, wherein said amlodipine and said atorvastatin are administered employing one drug delivery vehicle.

17. The method of claim 16, wherein said amlodipine and said atorvastatin are administered at different times.

18. The method of claim 16, wherein said amlodipine and said atorvastatin are administered at different times.

19. The method of claim 14, wherein said amlodipine and said atorvastatin are administered employing separate drug delivery vehicles.

20. The method of claim 14, wherein atorvastatin is a hemicalcium salt.

21. The method of claim 14, wherein amlodipine is a besylate salt.

22. The method of claim 14, wherein said amlodipine and said atorvastatin are administered employing one drug delivery vehicle.

23. The method of claim 14, wherein said amlodipine and said atorvastatin are administered employing separate drug delivery vehicles.

24. The method of claim 14, wherein atorvastatin is a hemicalcium salt.

* * * * *